US012594114B2

(12) United States Patent
Mcalpin

(10) Patent No.: US 12,594,114 B2
(45) Date of Patent: Apr. 7, 2026

(54) SURGICAL INSTRUMENT FOR COLORECTAL POLYP REMOVAL

(71) Applicant: Glenn Mark Mcalpin, Newnan, GA (US)

(72) Inventor: Glenn Mark Mcalpin, Newnan, GA (US)

( * ) Notice: Subject to any disclaimer, the term of this patent is extended or adjusted under 35 U.S.C. 154(b) by 1053 days.

(21) Appl. No.: 17/583,156

(22) Filed: Jan. 24, 2022

(65) Prior Publication Data

US 2022/0273357 A1 Sep. 1, 2022

Related U.S. Application Data

(63) Continuation-in-part of application No. 15/451,383, filed on Mar. 6, 2017, now abandoned.

(60) Provisional application No. 62/303,485, filed on Mar. 4, 2016.

(51) Int. Cl.
| | |
|---|---|
| *A61B 18/14* | (2006.01) |
| *A61B 1/018* | (2006.01) |
| *A61B 1/31* | (2006.01) |
| *A61B 10/06* | (2006.01) |
| *A61B 18/00* | (2006.01) |

(52) U.S. Cl.
CPC .......... *A61B 18/1445* (2013.01); *A61B 1/018* (2013.01); *A61B 1/31* (2013.01); *A61B 10/06* (2013.01); *A61B 2018/005* (2013.01); *A61B 2018/00595* (2013.01); *A61B 2018/00922* (2013.01); *A61B 2018/141* (2013.01)

(58) Field of Classification Search
CPC ....... A61B 18/1445; A61B 1/31; A61B 10/06; A61B 2018/005; A61B 2018/141; A61B 2017/320064; A61B 17/32056; A61B 2018/00601
See application file for complete search history.

(56) References Cited

U.S. PATENT DOCUMENTS

| | | | |
|---|---|---|---|
| 5,746,747 A | 5/1998 | McKeating | |
| 5,846,248 A * | 12/1998 | Chu ................. | A61B 17/32056 606/113 |
| 2005/0131403 A1 | 6/2005 | Chang | |
| 2006/0025780 A1* | 2/2006 | James .............. | A61B 17/32056 606/110 |
| 2007/0208339 A1 | 9/2007 | Arts et al. | |
| 2008/0015409 A1 | 1/2008 | Barlow et al. | |

(Continued)

FOREIGN PATENT DOCUMENTS

| | | |
|---|---|---|
| JP | 3743096 B2 | 2/2006 |
| WO | 39/10093 A1 | 11/1989 |
| WO | 01/10321 A1 | 2/2001 |

*Primary Examiner* — Alex M Valvis
*Assistant Examiner* — Yasmeen S Warsi
(74) *Attorney, Agent, or Firm* — Perilla Knox & Hildebrandt LLP; Stephanie Davy-Jow; Thomas Hildebrandt

(57) ABSTRACT

Disclosed are various embodiments of a surgical instrument for colorectal polyp removal. In various embodiment, the surgical instrument has an elongate flexible tubular sheath having a proximal end and a distal end, a snare having a loop and controlled by a pair of wires, and a biopsy forceps having a pair of jaws sized to fit within the loop of the snare. Both the biopsy forceps and the snare are routed through the elongate flexible tubular sheath so that the loop of the snare and the pair of jaws exit the distal end of the elongate flexible tubular sheath.

9 Claims, 6 Drawing Sheets

(56)             References Cited

U.S. PATENT DOCUMENTS

2011/0224492 A1     9/2011  Stern
2018/0028217 A1*    2/2018  Hassidov ........... A61B 18/1492

* cited by examiner

100

109

106    103

SURGICAL INSTRUMENT FOR COLORECTAL POLYP REMOVAL

CROSS-REFERENCE TO RELATED APPLICATIONS

This patent application is a continuation-in-part of U.S. patent application Ser. No. 15/451,383, filed Mar. 6, 2017, and titled "SURGICAL INSTRUMENT FOR COLOREC-TAL POLYP REMOVAL," which claims the benefit of U.S. Provisional Application No. 62/303,485, filed Mar. 4, 2016, and titled "SURGICAL INSTRUMENT FOR COLOREC-TAL POLYP REMOVAL," the entire contents of each application being hereby incorporated herein by reference.

BACKGROUND

A colorectal polyp is a fleshy growth occurring on the lining of the colon or rectum. Untreated colorectal polyps can develop into colorectal cancer. Polyps may be classified according to their behavior or etiology. Some may be benign, while others may be malignant. Polyps can be removed during a colonoscopy or sigmoidoscopy.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

The present disclosure relates to a surgical instrument that improves acquisition and removal of polyps, especially pedunculated polyps and some sessile polyps. Pedunculated polyps are those having a tubular appearance and attached to the intestinal wall by a stalk, while sessile polyps are those that are flat appearing and grow directly from the wall. Typically, polyps can be removed using a snare tool comprising a wire loop that cuts the stalk of the polyp and cauterizes it to prevent bleeding. However, using a snare tool alone often requires multiple attempts to remove a polyp.

Specifically, in one embodiment, a surgical instrument is disclosed that is a combination of a snare tool and biopsy (BX) forceps. The surgical instrument facilitates retrieval of an entire polyp without the multiple attempts usually required in using, for example, a snare tool alone. Removal of polyps with a snare tool may require multiple attempts due to the difficulty in placing the snare around the polyp completely. By placing BX forceps within the snare loop, this problem will be resolved. The BX forceps will retrieve and stabilize the entire polyp for snare placement and removal.

Figure 1:
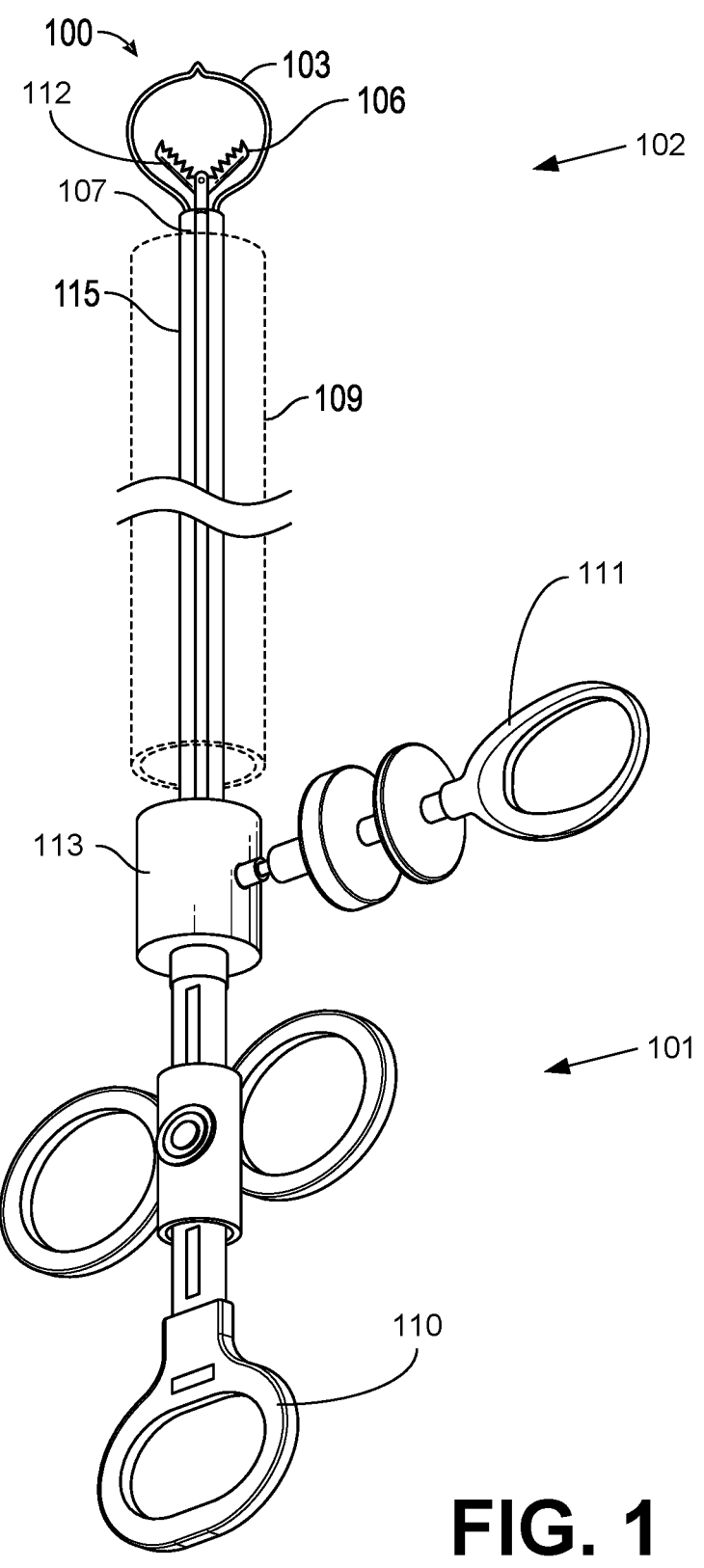
FIG. 1 is an example of a perspective view of a surgical instrument according to an embodiment of the present disclosure.

Referring now to FIG. 1, shown is an example of a perspective view of a surgical instrument 100 according to an embodiment of the present disclosure. The surgical instrument 100 has a proximal end 101 and a distal end 102. The surgical instrument 100 comprises a combination of a snare 103 and a BX forceps 106, within a shaft 107, which is configured to be placed within a plastic core 109 or elongate tubular member, such as a catheter sheath for endoscopy. The BX forceps 106 may be placed within the snare 103 loop. Otherwise, the BX forceps 106 may exit the core 109 alongside the snare 103.

The snare 103 and BX forceps 106 have separate coils and are able to move independently. Control handle 110 is used to control the snare 103, while control handle 111 is used to control the BX forceps 106.

The BX forceps 106 when activated is mobile (in and out) to grab the polyp using a pair of jaws 112. The wires of the snare 103 are made hot via a source of electrocautery current to perform the cauterization function of the polyp during removal. At 115, there is some stiffness to the wires to control the snare 103. It is noted that the snare 103 comprises two separate wires instead of one.

Figure 2:
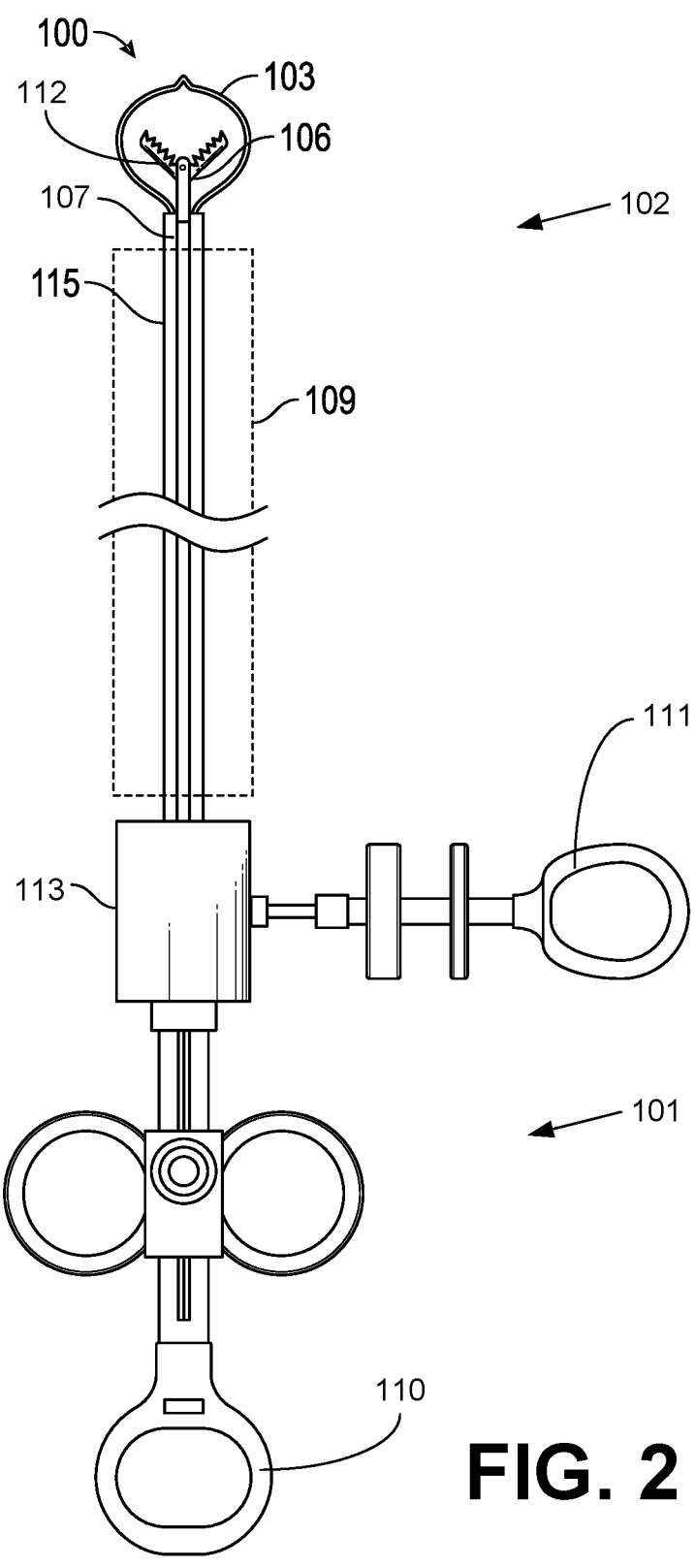
FIG. 2 is an example of a top view of the surgical instrument of FIG. 1 according to an embodiment of the present disclosure.
Figure 3A:
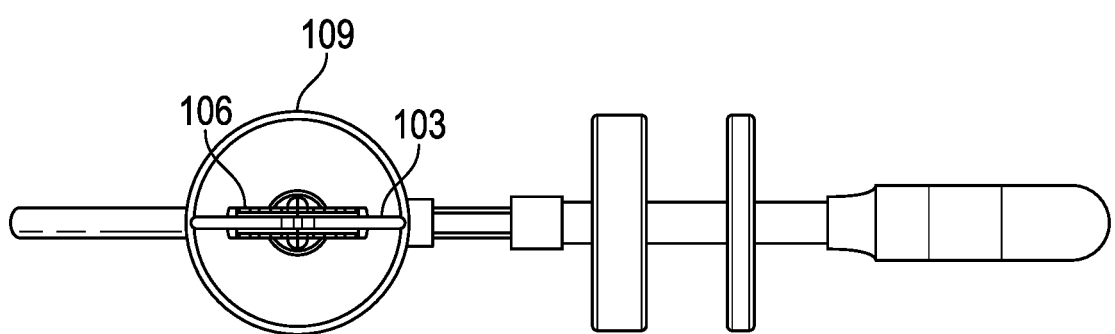
FIG. 3A is an example of an end view of the surgical instrument of FIG. 1 according to an embodiment of the present disclosure.

FIG. 2 provides a top view of the surgical instrument 100 according to an embodiment of the present disclosure. When the surgical instrument 100 is used in a surgical procedure, the surgical instrument 100 may be rotated about the longitudinal axis, and the use of a right angle provides a maximal distance between the two control handles 110, 111 that have different functions. FIG. 3A provides an end view of the plastic core 109, the snare 103, and the BX forceps 106.

Figure 3B:
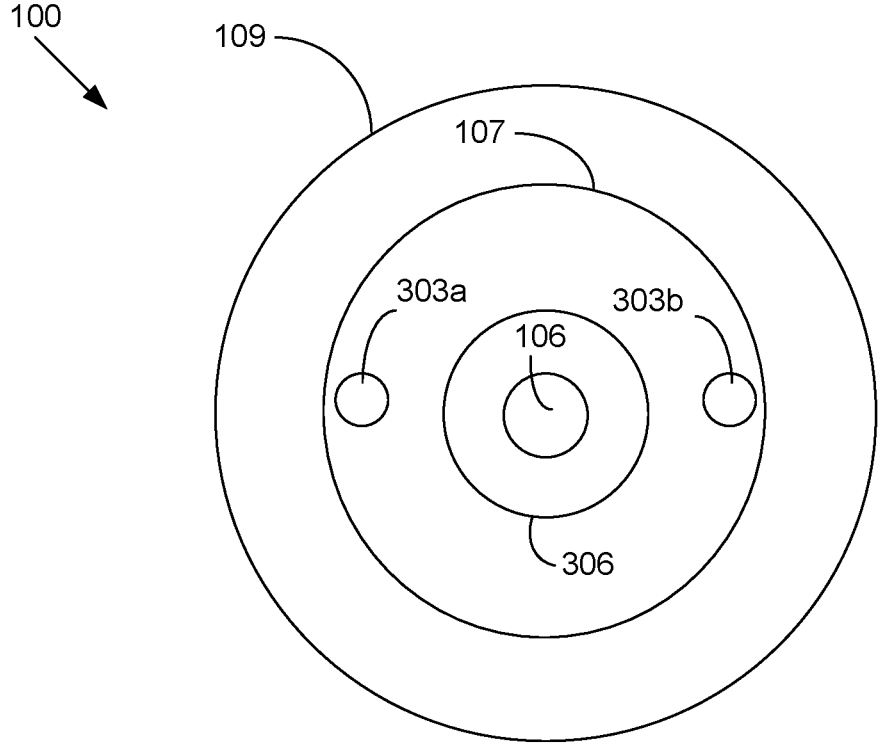
FIG. 3B is an example of a cross-sectional view of the surgical instrument of FIG. 1 according to an embodiment of the present disclosure.

FIG. 3B provides a cross-sectional view of the surgical instrument 100. In this view, the wires 303a and 303b for controlling the snare 103 (FIG. 1) are shown within the shaft 107, and the shaft 107 is within the sheath 109. A second coaxial sheath 306 is between the wires 303a and 303b, and inside the second sheath 306 is the control for the BX forceps 106. In this way, the BX forceps 106 is within the pair of wires 303a, 303b and oriented coaxially. This is in contrast to using two separate shafts for the snare 103 and the BX forceps 106 that could be passed through the sheath 109.

Figure 4:
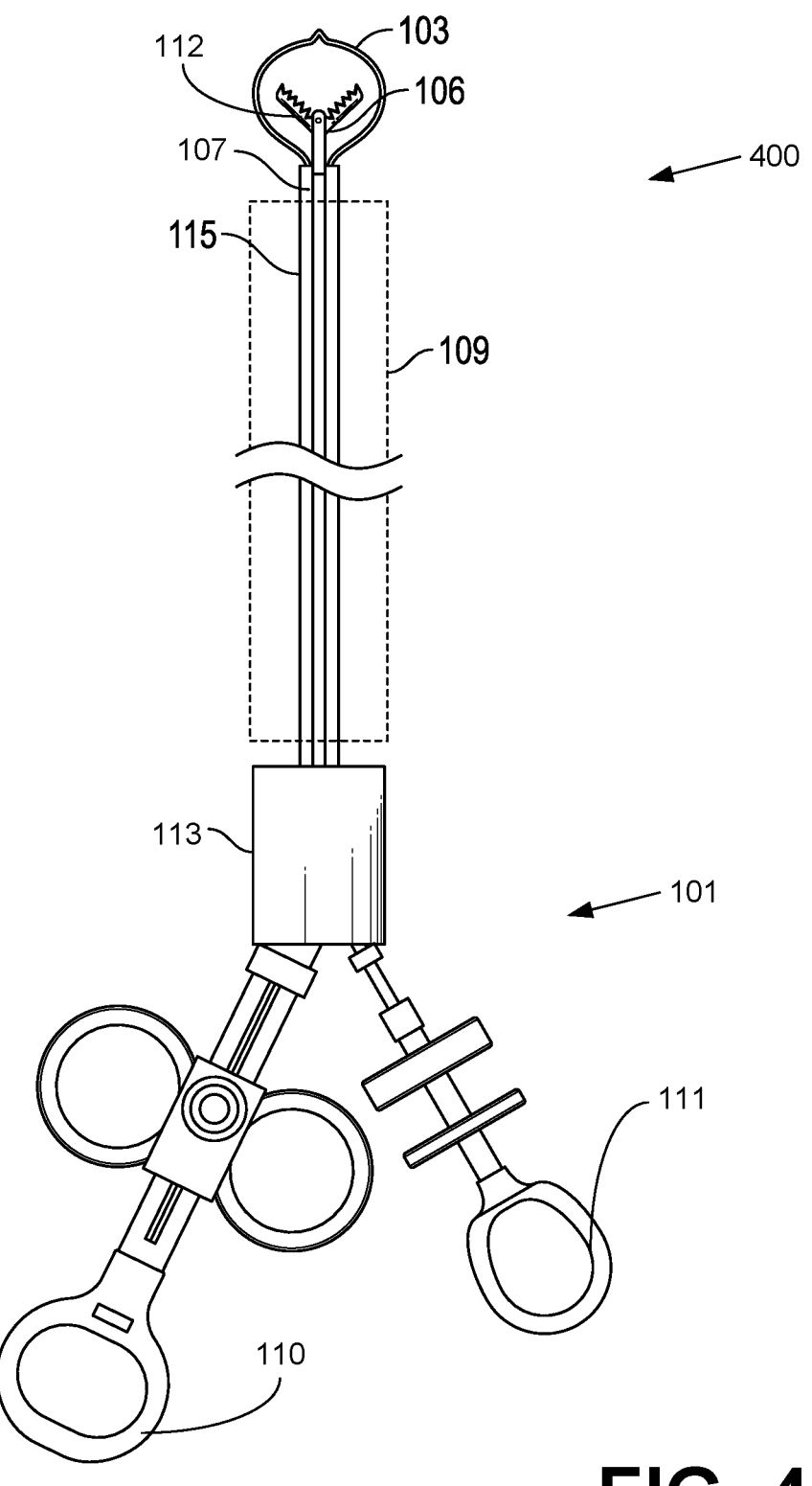
FIG. 4 provides a top view of a surgical instrument constituting a variation on the surgical instrument of FIG. 1 according to an embodiment of the present disclosure.

FIG. 4 provides a top view of a surgical instrument 400 constituting a variation on the surgical instrument 100. While in FIG. 2, the control handle 111 exits the shaft 107 at a right angle relative to the control handle 110, in FIG. 4, the control handles 110 and 111 are loosely coupled to the shaft 107.

Figure 5:
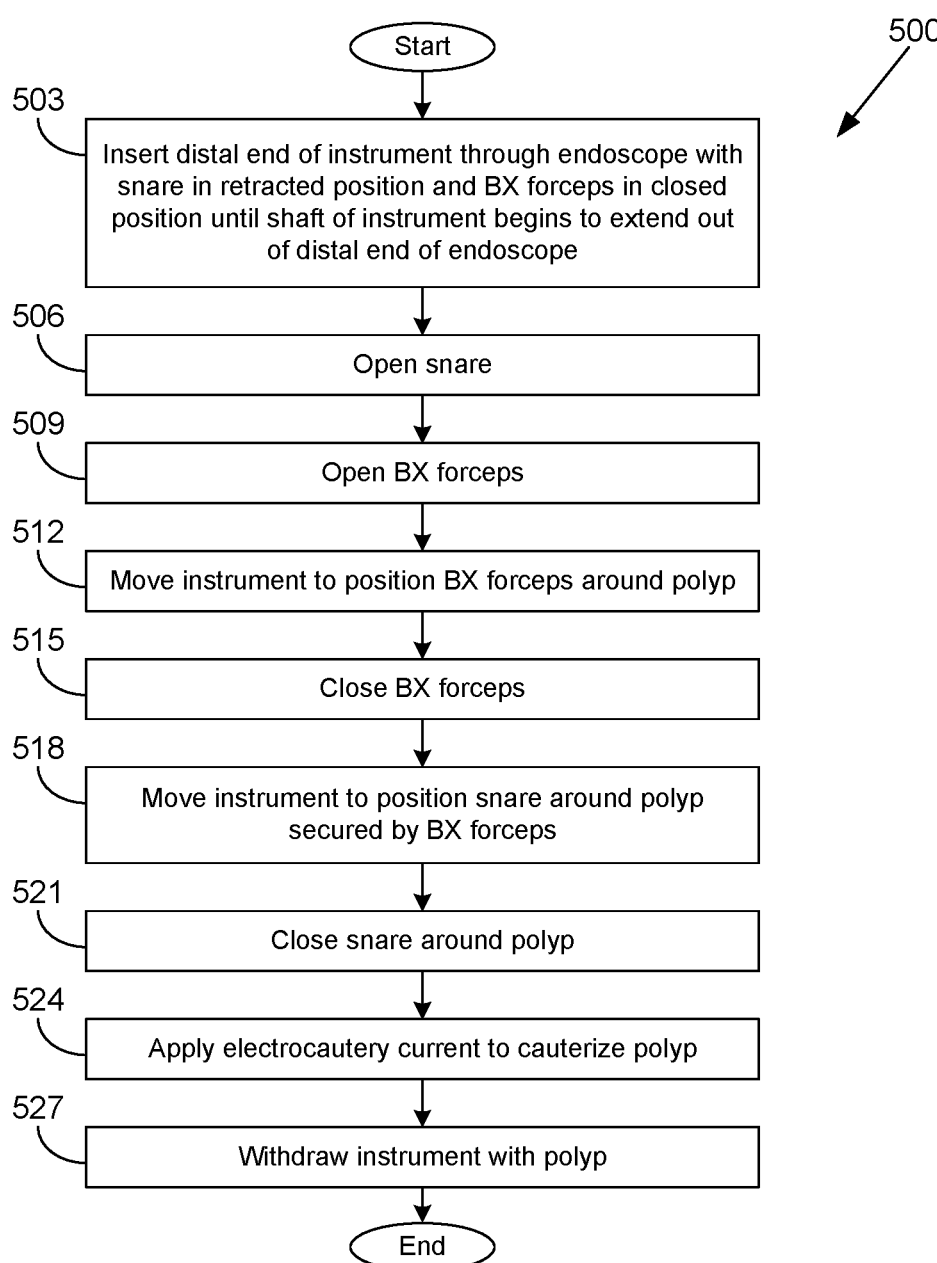
FIG. 5 is a flowchart depicting an example method of use for the surgical instrument of FIG. 1 according to an embodiment of the present disclosure.

FIG. 5 is a flowchart describing one example method of use 500 for the surgical instrument 100. At 503, the distal end 102 of the instrument 100 is inserted through an endoscope within the snare 103 in a retracted position and the BX forceps 106 in a closed position until the shaft 107 of the instrument 100 begins to extend out of the distal end of the endoscope. At 506, the snare 103 is opened using the control handle 110. At 509, the BX forceps 106 are opened using the control handle 111. At 512, the instrument 100 is moved to position the BX forceps 106 around a polyp. For example, the shaft 107 can be advanced and retracted into and out of the endoscope, while torque to the instrument 100 can be applied. At 515, the BX forceps 106 are closed using the control handle 111.

At 518, the instrument 100 is moved in order to position the snare 103 around the polyp, which is secured by the BX forceps 106. For example, the shaft 107 can be advanced and retracted into and out of the endoscope, while torque to the instrument 100 can be applied. At 521, the snare 103 is closed around the polyp using the control handle 110. At 524, electrocautery current is applied to desiccate, sever, and cauterize the polyp. At 527, the instrument 100 is withdrawn with the polyp being removed.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A method for polypectomy, comprising:
    inserting a distal end of a surgical instrument through an endoscope, the surgical instrument comprising:
    an elongate flexible tubular sheath having a proximal end and a distal end;
    a snare having a loop and controlled by a pair of wires, wherein the pair of wires is located within a shaft, wherein the shaft is located within the elongate flexible tubular sheath;
    a biopsy forceps having a pair of jaws sized to fit within and coplanar to the loop of the snare, wherein the biopsy forceps jaws are located between the loop of the snare and remain entirely within the loop of the snare in both open and closed positions during gripping; and
    wherein both the biopsy forceps and the snare are routed through the elongate flexible tubular sheath so that the loop of the snare and the pair of jaws exit the distal end of the elongate flexible tubular sheath, and a control for the biopsy forceps is coaxial and within the pair of wires such that the control for the biopsy forceps is within the shaft, and the snare is in a retracted position and the biopsy forceps is in a closed position;

opening the snare;
    opening the biopsy forceps;
    positioning the pair of jaws of the biopsy forceps around a polyp;
    closing the pair of jaws of the biopsy forceps on the polyp, thereby securing the polyp;
    positioning the loop of the snare around the polyp that has been secured by the biopsy forceps; and
    closing the loop of the snare around the polyp.

2. The method of claim 1, further comprising applying an electrocautery current to the snare to cauterize the polyp.

3. The method of claim 1, further comprising withdrawing the surgical instrument through the endoscope.

4. The method of claim 1, wherein the control for the biopsy forceps is within a second sheath that is coaxial and within the pair of wires, the second sheath being coaxial within the elongate flexible tubular sheath and inside the shaft.

5. The method of claim 1, wherein the elongate flexible tubular sheath is a first sheath and wherein the control for the biopsy forceps is within a second sheath that is coaxial and within the pair of wires, the second sheath being coaxial within the elongate flexible tubular sheath.

6. The method of claim 1, wherein a source of electrocautery current is coupled to the pair of wires of the snare, wherein when activated the electrocautery current causes the loop of the snare to heat.

7. The method of claim 1, wherein the surgical instrument further comprises a first control handle configured to control opening and closing of the loop of the snare, and a second control handle configured to control opening and closing of the pair of jaws of the biopsy forceps, wherein the first control handle is located at a proximal end of the surgical instrument and wherein the second control handle is positioned along a different axis from the first control handle.

8. The method of claim 7, wherein the second control handle is mounted on a lateral side of a rigid member, wherein an axis of the second control handle is at a right angle relative to the first control handle of the surgical instrument.

9. The method of claim 7, wherein the first control handle and the second control handle are loosely coupled at an opening at the proximal end of the elongate flexible tubular sheath.

* * * * *